(12) United States Patent
Nishimori et al.

(10) Patent No.: US 10,207,987 B2
(45) Date of Patent: Feb. 19, 2019

(54) POLYTHIOL COMPOSITION AND METHOD FOR PRODUCING SAME

(71) Applicant: MITSUBISHI GAS CHEMICAL COMPANY, INC., Tokyo (JP)

(72) Inventors: Yoshihiko Nishimori, Tokyo (JP); Kazuya Zenyoji, Tokyo (JP); Rie Sakata, Tokyo (JP); Teruo Kamura, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 48 days.

(21) Appl. No.: 15/310,279

(22) PCT Filed: Jul. 15, 2015

(86) PCT No.: PCT/JP2015/070231
§ 371 (c)(1),
(2) Date: Nov. 10, 2016

(87) PCT Pub. No.: WO2016/010065
PCT Pub. Date: Jan. 21, 2016

(65) Prior Publication Data
US 2017/0247322 A1 Aug. 31, 2017

(30) Foreign Application Priority Data

Jul. 18, 2014 (JP) .................... 2014-147702
Oct. 14, 2014 (JP) .................... 2014-209774

(51) Int. Cl.
| | | |
|---|---|---|
| G02B 1/04 | (2006.01) |
| C08G 75/04 | (2016.01) |
| C07C 319/28 | (2006.01) |
| C07C 321/10 | (2006.01) |
| C07C 321/14 | (2006.01) |

(52) U.S. Cl.
CPC .......... *C07C 319/28* (2013.01); *C07C 321/10* (2013.01); *C07C 321/14* (2013.01); *C08G 75/04* (2013.01); *G02B 1/04* (2013.01)

(58) Field of Classification Search
CPC ............ C08G 18/3876; C08G 18/7642; G02B 1/041; C07C 321/14; C08L 75/04; C08L 81/00
See application file for complete search history.

(56) References Cited

U.S. PATENT DOCUMENTS

| | | | |
|---|---|---|---|
| 2,312,688 A | 3/1973 | D'Alelio et al. |
| 2,324,284 A | 7/1973 | D'Alelio et al. |
| 5,087,758 A † | 2/1992 | Kanemura |
| 5,374,668 A | 12/1994 | Kanemura et al. |
| 5,608,115 A | 3/1997 | Okazaki et al. |
| 6,117,923 A | 9/2000 | Amagai et al. |
| 6,124,424 A | 9/2000 | Okazaki et al. |

| | | | |
|---|---|---|---|
| 2009/0264613 A1* | 10/2009 | Kuma ................. C07C 319/14 528/60 |
| 2015/0094443 A1† | 4/2015 | Kawaguchi |
| 2015/0126781 A1 | 5/2015 | Kawaguchi et al. |
| 2015/0133692 A1 | 5/2015 | Kawaguchi et al. |

FOREIGN PATENT DOCUMENTS

| | | |
|---|---|---|
| EP | 0378895 A | 7/1990 |
| EP | 2660260 A | 6/2013 |
| EP | 2845847 A | 3/2015 |
| EP | 3064488 A | 9/2016 |
| JP | 02-270859 | 11/1990 |
| JP | H09-136919 A | 5/1997 |
| JP | 10-298287 | 11/1998 |
| JP | 11-80308 | 3/1999 |
| JP | 11-124363 | 5/1999 |
| JP | 2006-003624 | 1/2006 |
| JP | 2006-124334 | 5/2006 |
| JP | 2006-131724 | 5/2006 |
| JP | 2006-284920 | 10/2006 |
| JP | 2010-083773 | 4/2010 |
| JP | 2011-231305 | † 11/2011 |
| JP | 2011-231305 A | 11/2011 |
| JP | 5319036 | 10/2013 |

(Continued)

OTHER PUBLICATIONS

Supplementary European Search Report issued in Patent Application No. 14854361.4, dated May 8, 2017.
Japanese Industrial Standards Committee; "Testing Methods for Industrial Water JIS0101: 1998", Published Apr. 20, 1998, pp. 1-5.
Office Action issued in U.S. Appl. No. 14/915,739, dated Oct. 18, 2016.
International Search Report issued in Patent Application No. PCT/JP2014/077303, dated Nov. 11, 2014.
International Search Report issued in Patent Application No. PCT/JP2015/070231, dated Oct. 20, 2015.

(Continued)

*Primary Examiner* — Shane Fang
(74) *Attorney, Agent, or Firm* — Greenblum & Bernstein, P.L.C.

(57) ABSTRACT

The present invention provides a polythiol composition containing, as the main component, a polythiol compound (a) having two or more mercapto groups, and containing 0.5% by mass or less of a nitrogen-containing compound (b) in which at least one mercapto group in the polythiol compound (a) is substituted with a group represented by formula (1).

(1)

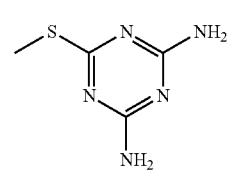

3 Claims, No Drawings

(56) References Cited

FOREIGN PATENT DOCUMENTS

| WO | 89/10575 | | 11/1989 |
| WO | 2003/002632 | | 1/2003 |
| WO | 2014/027427 | | 2/2014 |
| WO | 2014/027665 A | | 2/2014 |
| WO | 2015/064548 A | | 5/2015 |
| WO | 2014/027665 | † | 7/2016 |

OTHER PUBLICATIONS

Extended European Search Report in respect to European Application No. 15821668.9, dated Jan. 23, 2018.
Japanese Industrial Standards Committee; Testing Methods for Industrial Water; Pub: Apr. 20, 1998.†

\* cited by examiner
† cited by third party

POLYTHIOL COMPOSITION AND METHOD FOR PRODUCING SAME

TECHNICAL FIELD

The present invention relates to a polythiol composition, wherein the generation of a suspended matter is suppressed, a composition for optical materials comprising the polythiol composition, and an optical material obtained by polymerizing and curing the composition.

BACKGROUND ART

Plastic materials are lightweight, highly tough and easy to be dyed, and therefore are widely used for various types of optical materials. These optical materials are required to have low specific gravity, high transparency and low yellowness, and as optical properties, high refractive index, high Abbe number, etc. In order to satisfy these requirements, many compositions for optical materials comprising a sulfur-containing monomer, in particular, a polythiol compound have been developed (Patent Documents 1-2). However, in the case of the polythiol compounds described in the documents, an insoluble component (suspended matter) may be generated to cause turbidity during preservation, and white turbidity may be generated in resins obtained by polymerization and curing using these polythiol compounds.

PRIOR ART DOCUMENTS

Patent Documents

Patent Document 1: Japanese Laid-Open Patent Publication No. H02-270859
Patent Document 2: Japanese Laid-Open Patent Publication No. H10-298287

SUMMARY OF THE INVENTION

Problems to be Solved by the Invention

The problem to be solved by the present invention is to provide a polythiol composition for optical materials, wherein the generation of a suspended matter at the time of preservation of the polythiol composition is suppressed.

Means for Solving the Problems

The present inventors diligently made researches in order to solve the above-described problem, and found that the cause of the generation of a suspended matter is a nitrogen-containing compound (b), in which at least one mercapto group contained in a polythiol compound (a) having two or more mercapto groups is substituted with a group represented by general formula (1) below, and that decomposition thereof at the time of preservation affects the generation of the suspended matter.

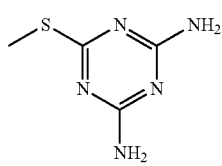

Specifically, the present invention is as follows:

<1> A method for producing a polythiol composition, which comprising purifying a polythiol composition containing, as the main component, a polythiol compound (a) having two or more mercapto groups, and containing more than 0.5% by mass of a nitrogen-containing compound (b) in which at least one mercapto group in the polythiol compound (a) is substituted with a group represented by formula (1) below:

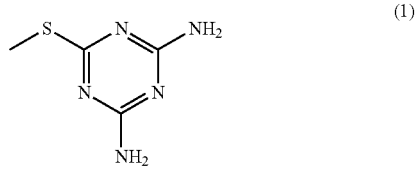

to produce a polythiol composition containing 0.5% by mass or less of the nitrogen-containing compound (b), wherein the purifying process has at least:

a process (1) of distilling the polythiol composition; and a process (2) of purifying the polythiol composition by a means other than distillation.

<2> The method for producing a polythiol composition according to item <1>, wherein the process (2) is carried out after the process (1).

<3> The method for producing a polythiol composition according to item <1>, wherein the process (2) is carried out before and after the process (1).

<4> The method for producing a polythiol composition according to any one of items <1> to <3>, wherein the means other than distillation is at least one means selected from water washing and acid washing.

<5> A method for producing a polythiol composition, which comprising purifying a polythiol composition containing, as the main component, a polythiol compound (a) having two or more mercapto groups, and containing more than 0.5% by mass of a nitrogen-containing compound (b) in which at least one mercapto group in the polythiol compound (a) is substituted with a group represented by formula (1) below:

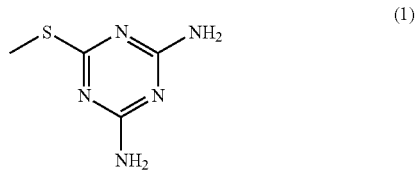

to produce a polythiol composition containing 0.5% by mass or less of the nitrogen-containing compound (b), wherein the purifying process has a process of washing the polythiol composition containing more than 0.5% by mass of the nitrogen-containing compound (b) with 6N or more of an acid.

<6> A method for producing a polythiol composition containing, as the main component, a polythiol compound (a) having two or more mercapto groups, and containing 0.5% by mass or less of a nitrogen-containing compound (b) in which at least one mercapto group in the polythiol compound (a) is substituted with a group represented by formula (1) below:

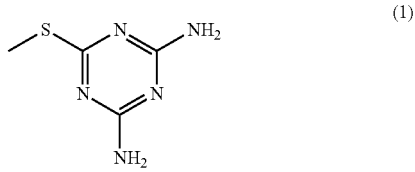

wherein the method has a process of hydrolyzing an isothiuronium salt that is a raw material of the polythiol compound (a) at 80° C. or higher.
<7> A polythiol composition containing, as the main component, a polythiol compound (a) having two or more mercapto groups, and containing 0.5% by mass or less of a nitrogen-containing compound (b) in which at least one mercapto group in the polythiol compound (a) is substituted with a group represented by formula (1) below:

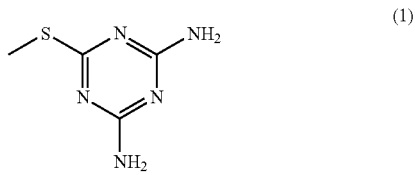

<8> The polythiol composition according to item <7>, wherein the polythiol compound (a) is obtained by hydrolyzing an isothiuronium salt.
<9> A polythiol composition produced by the method according to any one of items <1> to <6>.
<10> A composition for optical materials containing the polythiol composition according to any one of items <7> to <9>.
<11> An optical material obtained by polymerizing and curing the composition for optical materials according to item <10>.

Advantageous Effect of the Invention

By using the polythiol composition of the present invention, the generation of a suspended matter in the polythiol composition can be suppressed. Further, by polymerizing and curing a composition for optical materials comprising the polythiol composition of the present invention, an optical material excellent in color phase and transparency can be obtained.

EMBODIMENTS FOR CARRYING OUT THE INVENTION

The present invention relates to a polythiol composition containing, as the main component, a polythiol compound (a) having two or more mercapto groups, and containing 0.5% by mass or less of a nitrogen-containing compound (b) in which at least one mercapto group in the polythiol compound (a) is substituted with a group represented by the aforementioned formula (1). The content percentage of the polythiol compound (a) in the polythiol composition of the present invention is usually 75% by mass or more, preferably 80% by mass or more, and particularly preferably 85% by mass or more.

The polythiol compound (a) (hereinafter sometimes referred to as "the compound (a)") to be used in the present invention is not particularly limited as long as it is a compound having at least two mercapto groups in one molecule. Specific examples thereof include methanedithiol, 1,2-dimercaptoethane, 2,2-dimercaptopropane, 1,3-dimercaptopropane, 1,2,3-trimercaptopropane, 1,4-dimercaptobutane, 1,6-dimercaptohexane, bis(2-mercaptoethyl)sulfide, 1,2-bis(2-mercaptoethylthio)ethane, 1,5-dimercapto-3-oxapentane, 1,8-dimercapto-3,6-dioxaoctane, 2,2-dimethylpropane-1,3-dithiol, 3,4-dimethoxybutane-1,2-dithiol, 2-mercaptomethyl-1,3-dimercaptopropane, 2-mercaptomethyl-1,4-dimercaptopropane, 2-(2-mercaptoethylthio)-1,3-dimercaptopropane, 1,2-bis(2-mercaptoethylthio)-3-mercaptopropane, 1,1,1-tris(mercaptomethyl)propane, tetrakis(mercaptomethyl)methane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, ethyleneglycolbis(2-mercaptoacetate), ethyleneglycolbis(3-mercaptopropionate), 1,4-butanediolbis(2-mercaptoacetate), 1,4-butanediolbis(3-mercaptopropionate), trimethylolpropanetris(2-mercaptoacetate), trimethylolpropanetris(3-mercaptopropionate), pentaerythritoltetrakis(2-mercaptoacetate), pentaerythritoltetrakis(3-mercaptopropionate), 1,1-dimercaptocyclohexane, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-bis(mercaptomethyl)-1,4-dithiane, 2,5-bis(mercaptoethyl)-1,4-dithiane, 1,2-bis(mercaptomethyl)benzene, 1,3-bis(mercaptomethyl)benzene (also known as m-xylylene dithiol), 1,4-bis(mercaptomethyl)benzene, bis(4-mercaptophenyl)sulfide, bis(4-mercaptophenyl)ether, 2,2-bis(4-mercaptophenyl)propane, bis(4-mercaptomethylphenyl)sulfide, bis(4-mercaptomethylphenyl)ether and 2,2-bis(4-mercaptomethylphenyl)propane.

Among the above-described compounds, specific examples of preferred compounds include bis(2-mercaptoethyl)sulfide, pentaeryhiritoltetrakis(2-mercaptoacetate), pentaerythritoltetrakis(3-mercaptopropionate), 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, 1,3-bis(mercaptomethyl)benzene (also known as m-xylylene dithiol) and 1,4-bis(mercaptomethyl)benzene.

Specific examples of more preferred compounds include bis(2-mercaptoethyl)sulfide, 1,3-bis(mercaptomethyl)benzene, 1,2-bis[(2-mercaptoethyl)thio]-3-mercaptopropane and 1,1,3,3-tetrakis(mercaptomethylthio)propane, and the most preferred compounds are bis(2-mercaptoethyl)sulfide and 1,3-bis(mercaptomethyl)benzene (also known as m-xylylene dithiol). However, the compound (a) as the target of the present invention is not limited thereto.

The nitrogen-containing compound (b) (hereinafter sometimes referred to as "the compound (b)") contained in the polythiol composition of the present invention is a compound in which at least one mercapto group in the compound (a) is substituted with a group represented by the aforementioned formula (1). The content percentage of the compound (b) is preferably 0.5% by mass or less, more preferably 0.3% by mass or less, and even more preferably 0.05% by mass or less. The smaller the amount of the compound (b) is, the better, but in consideration of the purification cost, the content percentage is preferably 0.01% by mass or more. Meanwhile, when the amount of the compound (b) is large, a suspended matter tends to be easily generated at the time of preservation of the polythiol composition, and when polymerizing and curing a composition for optical materials comprising the polythiol composition, white turbidity occurs in a cured product.

In the present invention, examples of methods for reducing the amount of the compound (b) to 0.5% by mass or less include: a method in which a polythiol composition produced is washed with water and then distilled; a method in which a product obtained by purification by distillation is washed with water again; a method in which distillation is performed a plurality of times; and a method in which a polythiol composition is washed with an acid of 6N or more (preferably an acid of 6N to 12N) and then washed with water. Among them, preferred is a method in which distillation is combined with a purification means other than distillation, and more preferred is a method in which a purification means other than distillation is combined with distillation and performed after or before and after distillation. As the purification means other than distillation, acid washing or water washing is preferred. A method in which water washing is performed after distillation is particularly preferred. Further, it is preferred to reduce the amount of water after water washing by reducing pressure, heating, etc.

Moreover, examples of methods for reducing the amount of the compound (b) to 0.5% by mass or less also include a method in which hydrolysis of an isothiuronium salt that is a raw material of the polythiol compound (a) is performed at 80° C. or higher. The temperature for hydrolysis is more preferably 80 to 120° C. When the temperature is too high, oligomerization of a polythiol produced is caused, and therefore it is undesirable.

In the present invention, quantification of the compound (b) in the polythiol composition can be carried out by performing preparative GPC and measuring the weight as described in detail in the Examples below. Further, in the present invention, identification of the compound (b) in the polythiol composition can be carried out by accurate mass analysis according to LC-Tof-MS analysis and NMR analysis as described in detail in the Examples below.

The composition for optical materials of the present invention contains at least the aforementioned polythiol composition of the present invention. The composition for optical materials of the present invention may contain a polymerizable compound other than the polythiol compound. When obtaining an optical material by polymerizing and curing the composition for optical materials of the present invention, it is preferred to mix the composition for optical materials of the present invention with a polymerization catalyst and an additive, etc. according to need.

In addition, various publicly-known substances such as a chain extender, a crosslinking agent, a light stabilizer, an ultraviolet absorber, an antioxidant, an oil-soluble dye, a filler and an internal mold release agent may be added depending on purposes. A publicly-known reaction catalyst to be used in the production of polythiourethane for adjusting the reaction rate may also be suitably added. When producing an optical material such as a plastic lens from the composition for optical materials of the present invention, it is usually carried out by cast polymerization.

When producing the composition for optical materials of the present invention, it is preferred to carry out the defoaming treatment after mixing components. The degree of vacuum is 0.001 to 50 Torr, preferably 0.005 to 25 Torr, more preferably 0.01 to 10 Torr, and particularly preferably 0.1 to 5 Torr.

The composition for optical materials (cast molding solution) thus obtained can be purified by filtering impurities, etc. with a filter or the like immediately before polymerization and curing. It is desirable to filter impurities and the like from the composition for optical materials to be purified using a filter for further improving the quality of the optical material of the present invention. The pore diameter of the filter to be used herein is about 0.05 to 10 μm, and generally 0.1 to 1.0 μm. The material of the filter is preferably polytetrafluoroethylene (PTFE), polyethylene terephthalate (PET), polypropylene (PP) or the like.

The optical material of the present invention can be obtained by injecting the aforementioned composition for optical materials into a mold such as a glass mold and then polymerizing and curing the composition. The temperature and time for polymerization vary depending on the type of a monomer and additives, but the temperature is −10° C. to 160° C., and usually −10° C. to 140° C. The polymerization can be conducted by carrying out a step of holding the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps.

Further, it is preferred to anneal the material at a temperature of 50° C. to 150° C. for about 5 minutes to 5 hours after the polymerization is completed in terms of eliminating distortion of the optical material. Moreover, it can be subjected to a surface treatment such as dyeing, hard coating, antireflection treatment and imparting antifog properties, antifouling properties, impact resistance, etc. according to need.

EXAMPLES

Hereinafter, the present invention will be specifically described by way of working examples and comparative examples, but the present invention is not limited only to these working examples. Note that polythiol compositions obtained were evaluated according to the below-described methods.

Regarding quantification of the compound (b) in the polythiol composition, the below-described preparative GPC was performed and the weight was measured. Further, identification of the compound (b) was carried out by accurate mass analysis according to LC-Tof-MS analysis and NMR analysis.

Preparative GPC conditions
High speed liquid chromatography measurement conditions
Column: Jordi GEL DVB 500 Å (inner diameter: 10 mm, length: 250 mm, particle diameter: 5 μm)
Mobile phase: chloroform
Temperature: room temperature
Flow rate: 1.5 ml/min
Detector: UV detector, wavelength: 260 nm
Injection amount: 100 to 500 μL Note that conditions for high speed liquid chromatography are suitably selected according to the structures, physical properties, etc. of the polythiol compound (a) and the nitrogen-containing compound (b).

Evaluation of the Amount of a Suspended Matter in the Polythiol Composition 50 mL of the polythiol composition was put into a transparent glass bottle having a suitable size, and it was observed with a light being emitted from the side in a dark room. Regarding results, the case where there was almost no suspended matter was rated as A, the case where there was a slight amount of a suspended matter was rated as B, and the case where there was a large amount of a suspended matter was rated as C.

Comparative Example 1

Synthesis 1 of 1,3-bis(mercaptomethyl)benzene (Also Known as m-Xylylene Dithiol) (Compound a-1) Containing a Large Amount of the Compound (b)

In a 1 L four-neck reaction flask equipped with a stirring machine, a reflux cooling tube, a nitrogen gas purge tube and a thermometer, 74.1 g of m-xylylene dichloride, 67.2 g of thiourea and 270 g of water were mixed together, and the mixture was heated to reflux for 2.5 hours. The mixture was cooled to room temperature, and then 134.1 g of 50% aqueous solution of sodium hydroxide was added thereto under nitrogen atmosphere, and the mixture was hydrolyzed at 70° C. to 40° C. for 2 hours. Next, the reaction solution was cooled to 40° C., dilute hydrochloric acid was added thereto until pH became 3, and subsequently the mixture was stirred for 30 minutes to carry out neutralization. After the reaction was completed, extraction was carried out with 360 mL of toluene, and then toluene and a slight amount of water were removed under reduced pressure with heating, thereby obtaining 68.7 g of a polythiol composition containing m-xylylene dithiol. In this polythiol composition, the content percentage of the corresponding compound (b) was 1.0% by mass. Further, the content percentage of m-xylylene dithiol was 94.2% by mass.

Example 1

Synthesis 1 of m-Xylylene Dithiol (Compound a-1) Containing a Small Amount of the Compound (b)

In a 1 L four-neck reaction flask equipped with a stirring machine, a reflux cooling tube, a nitrogen gas purge tube and a thermometer, 74.1 g of m-xylylene dichloride, 67.2 g of thiourea and 270 g of water were mixed together, and the mixture was heated to reflux for 2.5 hours. The mixture was cooled to room temperature, and then 134.1 g of 50% aqueous solution of sodium hydroxide was added thereto under nitrogen atmosphere, and the mixture was hydrolyzed at 70° C. to 40° C. for 2 hours. Next, the reaction solution was cooled to 40° C., hydrochloric acid was added thereto until pH became 2, and subsequently the mixture was stirred for 30 minutes to carry out neutralization. After the reaction was completed, extraction was carried out with 360 mL of toluene, and then toluene and a slight amount of water were removed under reduced pressure with heating. After that, a polythiol composition containing m-xylylene dithiol obtained was purified by distillation, and then washed with water. The pressure was reduced with heating to remove water, and then filtration was carried out, thereby obtaining 55.0 g of a polythiol composition. In this polythiol composition, the content percentage of the corresponding compound (b) was 0.05% by mass. Further, the content percentage of m-xylylene dithiol was 99.6% by mass.

Example 2

Synthesis 2 of m-Xylylene Dithiol (Compound a-1) Containing a Small Amount of the Compound (b)

Synthesis was carried out in a manner similar to that in Example 1 to the step of extraction with toluene. After that, the toluene solution was washed with 6N hydrochloric acid and then water washing was carried out, and after that, toluene and a slight amount of water were removed under reduced pressure with heating. The weight of the obtained polythiol composition was 58.0 g. In this polythiol composition, the content percentage of the corresponding compound (b) was 0.07% by mass. Further, the content percentage of m-xylylene dithiol was 95.6% by mass.

Example 3

Synthesis 3 of m-Xylylene Dithiol (Compound a-1) Containing a Small Amount of the Compound (b)

Synthesis was carried out in a manner similar to that in Comparative Example 1, except that the temperature of hydrolysis was kept at 80° C. or higher, thereby obtaining 66.3 g of a polythiol composition containing m-xylylene dithiol. In this polythiol composition, the content percentage of the corresponding compound (b) was 0.32% by mass. Further, the content percentage of m-xylylene dithiol was 93.2% by mass.

Comparative Example 2

Synthesis of 1,2-bis[(2-mercaptoethyl)thio]-3-mercaptopropane (Compound a-2) Containing a Large Amount of the Compound (b)

76.0 g of water and 90.0 g (1.08 mol) of aqueous solution of sodium hydroxide (48% by mass) were put into a 2 L four-neck reaction flask equipped with a stirring machine, a reflux cooling tube, a nitrogen gas purge tube and a thermometer. 169 g (2.16 mol) of 2-mercaptoethanol was added dropwise thereto at 30° C. over 30 minutes, and after that, 99.9 g (1.08 mol) of epichlorohydrin was added dropwise thereto at the same temperature over 3 hours, and the mixture was matured for 1 hour. Next, 450.1 g (4.32 mol) of water containing hydrochloric acid (36% by mass) and 304.5 g (4.00 mol) of thiourea were added thereto, and the mixture was refluxed at 110° C. for 8 hours to provide a thiuronium salt. After it was cooled to 50° C., 450.0 g of toluene and 298 g (5.21 mol) of aqueous solution of ammonia (28% by mass) were added thereto to perform hydrolysis, thereby obtaining a toluene solution of polythiol containing 1,2-bis[(2-mercaptoethyl)thio]-3-mercaptopropane as the main component. The toluene solution was washed with water, and toluene and a slight amount of water were removed under reduced pressure with heating. After that, it was filtered, thereby obtaining 271.2 g of a polythiol composition containing a 1,2-bis[(2-mercaptoethyl)thio]-3-mercaptopropane compound as the main component. In this polythiol composition, the content percentage of the corresponding compound (b) was 1.2% by mass. Further, the content percentage of 1,2-bis[(2-mercaptoethyl)thio]-3-mercaptopropane was 82.3% by mass.

Example 4

Synthesis of 1,2-bis[(2-mercaptoethyl)thio]-3-mercaptopropane (Compound a-2) Containing Almost No Compound (b)

76.0 g of water and 90.0 g (1.08 mol) of aqueous solution of sodium hydroxide (48% by mass) were put into a 2 L four-neck reaction flask equipped with a stirring machine, a reflux cooling tube, a nitrogen gas purge tube and a thermometer. 169 g (2.16 mol) of 2-mercaptoethanol was added dropwise thereto at 30° C. over 30 minutes, and after that, 99.9 g (1.08 mol) of epichlorohydrin was added dropwise thereto at the same temperature over 3 hours, and the mixture was matured for 1 hour. Next, 450.1 g (4.32 mol) of water containing hydrochloric acid (36% by mass) and 304.5 g (4.00 mol) of thiourea were added thereto, and the mixture was refluxed at 110° C. for 8 hours to provide a thiuronium salt. After it was cooled to 50° C., 450.0 g of toluene and 298 g (5.21 mol) of aqueous solution of ammonia (28% by mass) were added thereto to perform hydrolysis, thereby obtaining a toluene solution of polythiol containing 1,2-bis[(2-mercaptoethyl)thio]-3-mercaptopropane as the main component. The toluene solution was washed with 1N acid and then with water, and toluene and a slight amount of water were removed under reduced pressure with heating. After that, a polythiol composition containing a 1,2-bis[(2-mercaptoethyl)thio]-3-mercaptopropane compound as the main component obtained was purified by distillation, and after that, it was washed with water again. Water was removed under reduced pressure with heating, and then filtration was carried out, thereby obtaining 235.4 g of a polythiol composition. In this polythiol composition, the content percentage of the corresponding compound (b) was 0.00% by mass. Further, the content percentage of 1,2-bis[(2-mercaptoethyl)thio]-3-mercaptopropane was 86.4% by mass.

Evaluation of Polythiol Composition

Examples 5 and 7

The polythiol compositions obtained in Example 1 and Comparative Example 1 were mixed together so that the amount of the compound (b) in the polythiol composition became the amount shown in Table 1. Subsequently, evaluation of suspended matter of the polythiol composition was carried out, and after that, as the acceleration test, the polythiol composition was preserved at 50° C. for 7 days. Finally, evaluation of suspended matter of the polythiol composition after preserved was carried out. The results are shown in Table 1.

Example 6

Evaluation was carried out in a manner similar to that in Example 5, except that the polythiol composition obtained in Example 3 was used directly. The results are shown in Table 1.

Example 8

Evaluation was carried out in a manner similar to that in Example 5, except that the polythiol composition obtained in Example 2 was used directly. The results are shown in Table 1.

Example 9

Evaluation was carried out in a manner similar to that in Example 5, except that the polythiol composition obtained in Example 1 was used directly. The results are shown in Table 1.

Examples 10 and 11

The polythiol compositions produced in Example 4 and Comparative Example 2 were mixed together so that the amount of the compound (b) in the polythiol composition became the amount shown in Table 1, and then evaluation was carried out in a manner similar to that in Example 5. The results are shown in Table 1.

Comparative Examples 3-5

In a manner similar to that in Examples 5 and 10, mixing was carried out so that the amount of the compound (b) in the polythiol composition became the amount shown in Table 1, and then evaluation was carried out in a manner similar to that in Example 5. The results are shown in Table 1.

Comparative Example 6

Synthesis 2 of m-Xylylene Dithiol (Compound a-1) Containing a Large Amount of the Compound (b) and Evaluation of Polythiol Composition Synthesis was carried out in a manner similar to that in Example 1 to the step of extraction with toluene. After that, the toluene solution was washed with 1N acid and then washed with water 3 times, and after that, toluene and a slight amount of water were removed under reduced pressure with heating (purification by distillation was not performed). The weight of the obtained polythiol composition was 67.4 g. In this polythiol composition, the content percentage of the corresponding compound (b) was 0.75% by mass. Further, the content percentage of m-xylylene dithiol was 94.9% by mass.

Evaluation was carried out in a manner similar to that in Example 5, except that the obtained polythiol composition was used directly. The results are shown in Table 1.

Comparative Example 7

Synthesis 3 of m-Xylylene Dithiol (Compound a-1) Containing a Large Amount of the Compound (b) and Evaluation of Polythiol Composition Synthesis was carried out in a manner similar to that in Example 1, except that water washing after distillation was not performed. The weight of the obtained polythiol composition was 56.2 g. In this polythiol composition, the content percentage of the corresponding compound (b) was 0.56% by mass. Further, the content percentage of m-xylylene dithiol was 98.6% by mass.

Evaluation was carried out in a manner similar to that in Example 5, except that the obtained polythiol composition was used directly. The results are shown in Table 1.

TABLE 1

| | Compound (a) | Compound (b) in composition (% by mass) | Initial stage | After preserved at 50° C. for 7 days |
|---|---|---|---|---|
| Example 5 | a-1 | 0.48 | A | B |
| Example 6 | a-1 | 0.32 | A | B |
| Example 7 | a-1 | 0.15 | A | A |
| Example 8 | a-1 | 0.07 | A | A |
| Example 9 | a-1 | 0.05 | A | A |
| Example 10 | a-2 | 0.48 | A | A |
| Example 11 | a-2 | 0.01 | A | A |
| Comparative Example 3 | a-1 | 0.90 | C | C |
| Comparative Example 4 | a-1 | 0.55 | B | C |

TABLE 1-continued

| | Compound (a) | Compound (b) in composition (% by mass) | Initial stage | After preserved at 50° C. for 7 days |
|---|---|---|---|---|
| Comparative Example 5 | a-2 | 0.82 | B | C |
| Comparative Example 6 | a-1 | 0.75 | B | C |
| Comparative Example 7 | a-1 | 0.56 | B | C |

Evaluation of Suspended Matter

A: There was almost no suspended matter.

B: There was a slight amount of a suspended matter. The level at which there is no quality problem.

C: There was a large amount of a suspended matter.

Compound (a)

a-1: m-xylylene dithiol a-2: 1,2-bis[(2-mercaptoethyl)thio]-3-mercaptopropane

The invention claimed is:

1. A method for producing a polythiol composition, the method comprising purifying a polythiol composition containing, as the main component, a polythiol compound (a) having two or more mercapto groups, and containing more than 0.5% by mass of a nitrogen-containing compound (b) in which at least one mercapto group in the polythiol compound (a) is substituted with a group represented by formula (1) below:

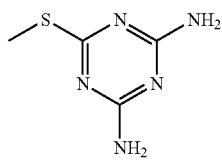
(1)

to produce a polythiol composition containing 0.01% by mass to 0.5% by mass of the nitrogen-containing compound (b), wherein the purifying process has at least:

a process (1) of distilling the polythiol composition; and a process (2) of purifying the polythiol composition by water washing and/or acid washing, wherein the process (2) is carried out after the process (1).

2. The method for producing a polythiol composition according to claim 1, wherein the process (2) is further carried out before the process (1).

3. A method for producing a polythiol composition, the method comprising purifying a polythiol composition containing, as the main component, a polythiol compound (a) having two or more mercapto groups, and containing more than 0.5% by mass of a nitrogen-containing compound (b) in which at least one mercapto group in the polythiol compound (a) is substituted with a group represented by formula (1) below:

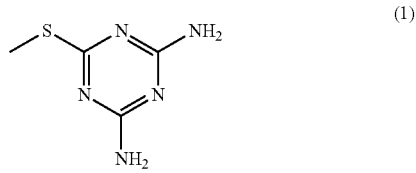
(1)

to produce a polythiol composition containing 0.01% by mass to 0.5% by mass of the nitrogen-containing compound (b), wherein the purifying process has a process of washing the polythiol composition containing more than 0.5% by mass of the nitrogen-containing compound (b) with 6N or more of an acid.

* * * * *